(12) United States Patent
Halpern et al.

(10) Patent No.: US 10,086,192 B2
(45) Date of Patent: Oct. 2, 2018

(54) NEURAL INTERFACE INSERTION AND RETRACTION TOOLS

(71) Applicant: Modular Bionics Inc., Santa Ana, CA (US)

(72) Inventors: Ian Loren Halpern, San Francisco, CA (US); Mark William Merlo, Santa Ana, CA (US)

(73) Assignee: Modular Bionics Inc., Berkeley, CA (US)

(*) Notice: Subject to any disclaimer, the term of this patent is extended or adjusted under 35 U.S.C. 154(b) by 55 days.

(21) Appl. No.: 15/204,935

(22) Filed: Jul. 7, 2016

(65) Prior Publication Data

US 2018/0008819 A1    Jan. 11, 2018

(51) Int. Cl.
*A61N 1/05* (2006.01)
*A61N 1/36* (2006.01)
*A61B 17/00* (2006.01)

(52) U.S. Cl.
CPC ...... *A61N 1/0529* (2013.01); *A61B 17/00234* (2013.01); *A61N 1/3605* (2013.01); *A61B 2017/00345* (2013.01)

(58) Field of Classification Search
CPC ... A61B 5/0478; A61B 5/685; A61B 5/04001; A61B 2560/0219; A61B 2562/046; A61N 1/0558; A61N 1/0502; A61N 1/0529; A61N 1/053
USPC .................................................. 600/378, 544
See application file for complete search history.

(56) References Cited

U.S. PATENT DOCUMENTS

| | | | |
|---|---|---|---|
| 4,207,903 A | 6/1980 | O'Neill | |
| 4,213,465 A | 7/1980 | Renheim | |
| 4,441,498 A | 4/1984 | Nordling | |
| 4,461,304 A | 7/1984 | Kuperstein | |
| 4,573,481 A | 3/1986 | Bullara | |
| 4,640,983 A | 2/1987 | Comte | |
| 4,920,979 A | 5/1990 | Bullara | |
| 4,964,414 A | 10/1990 | Handa et al. | |
| 5,215,088 A | 6/1993 | Normann et al. | |

(Continued)

FOREIGN PATENT DOCUMENTS

| | | |
|---|---|---|
| EP | 1985579 | 10/2008 |
| WO | WO 2010/138228 | 12/2010 |
| WO | WO 2013/096873 | 6/2013 |

OTHER PUBLICATIONS

U.S. Appl. No. 15/192,905, filed Jun. 24, 2016, Halpern et al.

(Continued)

*Primary Examiner* — Carl H Layno
*Assistant Examiner* — Jon Eric C Morales
(74) *Attorney, Agent, or Firm* — Knobbe, Martens, Olson & Bear, LLP (57) ABSTRACT

Devices and methods for manipulating devices such as micro-scale devices are provided. The devices can include a tether of various materials surrounded by a stiff body. The tether interfaces with microscale devices to draw them against the stiff body, holding the microscale devices in a locked position for insertion into or extraction out of tissue. The tensional hook and stiff body are configurable in a multitude of positions and geometries to provide increased engagement. Such configurations allow for a range of implantation and extraction surgical procedures for the device within research and clinical settings.

45 Claims, 4 Drawing Sheets

(56) References Cited

U.S. PATENT DOCUMENTS

| | | | |
|---|---|---|---|
| 5,361,760 | A | 11/1994 | Normann et al. |
| 5,938,689 | A | 8/1999 | Fischell et al. |
| 6,002,957 | A | 12/1999 | Finneran |
| 6,009,350 | A | 12/1999 | Renken |
| 6,304,785 | B1 | 10/2001 | McCreery et al. |
| 6,456,256 | B1 | 9/2002 | Amundson et al. |
| 6,560,479 | B2 | 5/2003 | van Drongelen |
| 6,719,582 | B1 | 4/2004 | Swanson |
| 6,829,498 | B2 | 12/2004 | Kipke et al. |
| 6,965,794 | B2 | 11/2005 | Brody |
| 7,006,859 | B1 | 2/2006 | Osorio et al. |
| 7,010,356 | B2 | 3/2006 | Jog et al. |
| 7,149,578 | B2 | 12/2006 | Edvardsson |
| 7,162,310 | B2 | 1/2007 | Doan |
| 7,203,548 | B2 | 4/2007 | Whitehurst et al. |
| 7,212,851 | B2 | 5/2007 | Donoghue et al. |
| 7,299,089 | B2 | 11/2007 | Wolf et al. |
| 7,460,904 | B2 | 12/2008 | Deadwyler et al. |
| 7,548,775 | B2 | 6/2009 | Kipke et al. |
| 7,729,758 | B2 | 6/2010 | Haller et al. |
| 7,751,877 | B2 | 7/2010 | Flaherty et al. |
| 7,805,175 | B2 | 9/2010 | Lin et al. |
| 7,991,475 | B1 | 8/2011 | Tang et al. |
| 8,024,022 | B2 | 9/2011 | Schulman et al. |
| 8,027,735 | B1 | 9/2011 | Tzivskos et al. |
| 8,086,322 | B2 | 12/2011 | Schouenborg |
| 8,090,448 | B2 | 1/2012 | Greenberg et al. |
| 8,112,160 | B2 | 2/2012 | Foster |
| 8,160,696 | B2 | 4/2012 | Bendett et al. |
| 8,255,061 | B2 | 8/2012 | Perlin et al. |
| 8,774,937 | B2 | 7/2014 | Mercanzini et al. |
| 8,958,868 | B2 | 2/2015 | Ghovanloo et al. |
| 9,095,267 | B2 | 8/2015 | Halpern et al. |
| 9,240,630 | B2 | 1/2016 | Joshi |
| 2004/0082875 | A1 | 4/2004 | Donoghue et al. |
| 2004/0199235 | A1 | 10/2004 | Younis |
| 2005/0021117 | A1 | 1/2005 | He et al. |
| 2006/0173263 | A1 | 8/2006 | He et al. |
| 2007/0191906 | A1 | 8/2007 | Iyer et al. |
| 2009/0099441 | A1 | 4/2009 | Giszter et al. |
| 2009/0112278 | A1 | 4/2009 | Wingeier et al. |
| 2009/0157141 | A1 | 6/2009 | Chiao et al. |
| 2009/0177144 | A1 | 7/2009 | Masmanidis et al. |
| 2010/0178810 | A2 | 7/2010 | Aarts et al. |
| 2010/0198281 | A1 | 8/2010 | Chang et al. |
| 2010/0292759 | A1 | 11/2010 | Hahn et al. |
| 2011/0144467 | A1 | 6/2011 | Yao et al. |
| 2011/0144639 | A1 | 6/2011 | Govari |
| 2012/0083719 | A1 | 4/2012 | Mishelevich |
| 2012/0123289 | A1 | 5/2012 | Sorenson et al. |
| 2012/0203129 | A1 | 8/2012 | Rennaker |
| 2012/0302856 | A1 | 11/2012 | Chang et al. |
| 2013/0172717 | A1* | 7/2013 | Halpern ............... A61B 5/0478 600/378 |
| 2014/0094674 | A1 | 4/2014 | Nurmikko et al. |
| 2015/0335883 | A1 | 11/2015 | Halpern et al. |

OTHER PUBLICATIONS

Barna, James S., et al., "A New Multielectrode Array for the Simultaneous Recording of Field Potentials and Unit Activity", Electroencephalography and Clinical Neurophysiology 1981, 52: pp. 494-496.

International Search Report Dated Apr. 4, 2013 for PCT App. No. PCT/US2012/071429 in 8 pages.

Jellema et al. "A slim needle-shaped multiwire microelectrode for intracerebral recording." J. Neurosci. Methods, 40 (1991) 203-209.

Karmos, George, et al., "A New Multielectrode for Chronic Recording of Intracortical Field Potentials in Cats", Physiology Behavior, 1982, vol. 29, pp. 567-570.

Nicolelis, Miguel A.L., "Methods for Neural Ensemble Recordings", CRC Press LLC, 1999, pp. 5-12 in 10 pages.

Plexon Neurotechnology Research Systems, V-Probe Technical Guide 8, 16, 24 and 32 Channels (2013) in 14 pages.

Ulbert, Dr. Istvan, "Investigation of the evoked and spontaneous intracortical electrical activity with multielectrodes in humans", Semmelweis University Doctoral School, Neurosciences, Budapest, 2001, in 101 pages.

Ulbert, Istvan, "Multiple channel microelectrode system for human epilepsy research", IEEE, 2006, pp. 222-225.

Ulbert, Istvan, et al., "In vivo laminar electrophysiology co-registered with histology in the hippocampus of patients with temporal lobe epilepsy", Experimental Neurology, 187 (2004), pp. 310-318.

Ulbert, Istvan, et al., "Multiple microelectrode-recording system for human intracortical applications", Journal of Neuroscience Methods, 106 (2001) 69-79.

* cited by examiner

Fig. 1

NEURAL INTERFACE INSERTION AND RETRACTION TOOLS

STATEMENT REGARDING FEDERALLY SPONSORED R&D

This invention was made with government support under NIH Grant/Federal Identifier Number R43NS081837 awarded by the National Institutes of Health of the United States of America. The government may have certain rights in the invention.

BACKGROUND

Some aspects of the present invention relates generally to tools used to implant and remove neural interface devices within nervous systems. More particularly, some embodiments of the invention relates to device systems that can be used to insert and retract a range of microscale devices dependent upon the desired research or clinical purpose.

SUMMARY

Disclosed herein is a method of inserting a micro-scale device into a target substrate. The method can include, in some embodiments, providing an insertion tool comprising a tether having a proximal end, a distal end, and an elongate body, and an end effector operably connected to the distal end of the tether. The method can also include mechanically coupling the end effector to a portion of the micro-scale device. The method can also include positioning the micro-scale device at a desired location within a target substrate. The method can further include mechanically decoupling the end effector from the micro-scale device. Also, the method can include withdrawing the insertion tool from the target substrate. In some embodiments, positioning the micro-scale device at a desired location includes moving the end effector distally with respect to a housing of the insertion tool. The housing can include, for example, a tubular body that includes a central lumen. The end effector can include a hook on its distal end, and/or a releasable connector. At smaller scales, the end effector can be pushed like a rod and pulled in tension like a cable. The micro-scale device can include, for example, a neural and/or biological interface.

In some embodiments, mechanically coupling the end effector to a portion of the micro-scale device can include positioning the hook through an aperture, hook-like structure, or other complementary element on the micro-scale device. Mechanically decoupling the end effector to a portion of the micro-scale device can include disassociating the hook from an aperture on the micro-scale device. In some embodiments, the target substrate is non-stationary, and can include neural tissue. In some embodiments, mechanically coupling the end effector to a portion of the micro-scale device does not substantially displace the micro-scale device.

The method can also include, in some embodiments, monitoring the motion of the nonstationary target surface. Positioning the micro-scale device can also include adjusting the positioning speed as a function of the monitored motion of the target surface. Positioning can also include manipulating a tab on the end effector. In some embodiments, positioning the micro-scale device comprises actuating a control on the proximal end of the device to move the tether with respect to the elongate body. Actuating a control can also include rotating a control knob in a direction, thereby moving a tracking pin axially distally within a slot oriented substantially parallel to the longitudinal axis of the elongate body. The tether can be elastic or inelastic, and the sidewall of the aperture can be elastic in some embodiments.

In some embodiments, disclosed is a tool configured for inserting and retracting a micro-scale device. The tool can include one or more of a housing, a tether including a proximal end, a distal end, and an elongate body. A portion of the tether can be configured to extend distally from the housing in a first configuration and be retracted within the housing in a second configuration. The tool can also include an end effector operably connected to the distal end of the tether, the end effector configured to reversibly mechanically couple with a portion of the micro-scale device. The tool can be configured such that the mechanical coupling does not substantially displace the micro-scale device. The housing can include a tubular body. The tether is configured to slide within a channel of the housing. The end effector can include, in some cases, a hook, and a pivoting joint connected to the hook. The end effector can also include one, two, or more laterally-extending tabs configured to allow a user to position the micro-scale device within a target location. The end effector can also include an aperture near a proximal end of the end effector. The aperture can be configured to house a portion of the tether therethrough, thereby coupling the end effector and the tether. In some embodiments, the tubular body can include a slot oriented axially with respect to a longitudinal axis of the tubular body. The tool can be configured to insert and retract a neural array. The end effector can also be threaded through an aperture on a micro-scale device. In some embodiments, the proximal end of the housing can include a control knob operably connected to and configured to actuate the tether proximally or distally with respect to the housing. The tool can also include a slot on the housing, and can be oriented substantially parallel to a longitudinal axis of the housing. The tool can also include a pin oriented axially or radially on an inner member, such as an inner tubular member, and configured to slide in a direction, such as axially, with respect to the housing. The pin can be configured to move axially within the slot. The tether can be elastic or inelastic.

In some embodiments, disclosed herein is a neural interface delivery system, including an insertion and removal tool, and a neural interface and/or biological interface. In some embodiments, the neural microarray can include a flexible baseplate, at least one microelectrode, and a loop on the flexible baseplate configured to reversibly couple with the end effector of the insertion and removal tool.

Also disclosed herein is a method of removing a micro-scale device from a target substrate. The method can include, for example, providing an removal tool comprising a tether having a proximal end, a distal end, and an elongate body, and an end effector operably connected to the distal end of the tether; mechanically coupling the end effector to a portion of the micro-scale device embedded at least partially within the target substrate; and withdrawing the insertion tool and the micro-scale device from the target substrate.

DETAILED DESCRIPTION

Neural interfaces are implanted within the nervous systems of animals and humans to record, stimulate, and treat neural tissue activity. Typically, this occurs within animal research of a variety of fields (e.g. neurological disorders and basic nervous system function) as well as clinical diagnosis and therapy (e.g., epilepsy).

Neural interfaces are implanted through a variety of methods, and are held during insertion by a variety of means including vacuum, mechanical lock, adhesive, dissolvable adhesive, and momentary impulse contact. The most pervasive form of holding microscale devices for insertion is a stiff engagement of some kind with a separate device such as a micro-positioner. It can be advantageous as it keeps delicate microscale devices stiff during insertion into dynamic tissue and allows a range of insertion speeds. Impulse insertion is also popular for microscale devices with large number of shanks. Impulse inserters are most commonly formed from metal and polymer components and powered using pneumatics. The procedure of impulse insertion positions a cabled microscale device over targeted tissue. The impulse inserter is then placed over the microscale device. The impulse inserter then receives a pneumatic pulse that actuates the insertion mechanism, striking the microscale device at a high rate of speed and sending it into the neural tissue.

Unfortunately, the impulse process requires a high degree of skill to position the microscale device and impulse inserter as well as actuate the inserter at the appropriate time. The average researcher is incapable of using the technique without significant training and often relies on an outsider with special expertise in impulse insertion. Mechanically locked insertion is a poor solution for implanting microscale devices for chronic experiments or periods. Microscale devices meant for chronic implantation often have cables to implanted structures. These cables are both delicate and resilient; they are easy to plastically deform to the point of damage, and if deflected too far during insertion can apply a residual force on the implanted microscale device, resulting in damage to tissue over time. Basic assembly to microscale devices with cables is also challenging during surgeries as the cables leading out of microscale devices terminate in large connectors which are affixed to tissue; the microscale devices are then adjusted with small deflections of the cable until positioned over the target tissue. This process leaves little room for additional deflection of the cable, increasing the requirement for flexibility of the insertion device or insertion technique.

These limitations prevent the implantation of chronic neural interfaces in a wide variety of situations. This reduces the amount of data acquired as well as limiting current and future therapies. Current insertion techniques also limit the visibility of the electrode for the researcher.

Accordingly, in some embodiments, disclosed herein is an insertion and extraction device that manipulates micro-scale devices, and provides unlimited degrees of freedom for placing and removing micro-scale devices. In some embodiments, the insertion and extraction device may have a tensional hook for engaging with micro-scale devices. It can also be advantageous to have a tensional loop. By using a loop, the corresponding hook on an implanted micro-scale device might be easier to extract after a lengthy implantation that encapsulated the device in tissue. In some embodiments, the insertion and/or retraction device may have a spring and dampening system to compensate for deflection of tissue during respiration. In other embodiments, the insertion and/or retraction device is actively positioned to follow the motion of tissue. In some embodiments, the insertion and/or retraction device uses a computer to monitor the motion of the tissue and adjusts the speed and deflection of the mechanical device accordingly within a closed loop feedback system.

An insertion and/or retraction device capable of interfacing with a flexible baseplate (e.g., joining body) can also be advantageous in some embodiments as it allows customization of placement within the nervous system and increased conformity to anatomical variations for research and clinical applications. In some embodiments, the joining body is configured to be flexible enough to bend around the outer curvature of neural tissue (e.g., sulcus surface of cortex, circumference of a nerve, or surface of a plexus). In some embodiments the joining body is configured to be flexible enough to bend with the motion of neural tissue due to respiration or containing body acceleration and deceleration.

In some embodiments, disclosed herein is an insertion and/or retraction device to manipulate various devices, including but not limited to implantable medical devices. The device to be inserted and/or removed can be a micro-scale device in some embodiments, but is not necessarily limited to devices to be inserted and/or retracted of a particular size. In some embodiments, the devices to be inserted and/or removed with systems and methods as disclosed herein can have a device total volume of about or less than about, for example, 100 mm$^3$, 50 mm$^3$, 25 mm$^3$, 10 mm$^3$, 5 mm$^3$, 2 mm$^3$, 1 mm$^3$, 0.5 mm$^3$, 0.25 mm$^3$, 0.1 mm$^3$, 0.05 mm³, or less. In some embodiments. the device to be inserted and/or removed could be, for example, an implantable neural interface device. In some embodiments, the device to be inserted has dimensions of about 1 mm×1 mm×1 mm or smaller. Neural interface devices as referred to herein could involve brain or spinal cord devices, but also peripheral nerve devices including sympathetic and parasympathetic nerves, as well as devices that monitor and/or treat cardiac and other tissues. The insertion and/or retraction device can interface with various types of micro-scale devices, including but not limited to neural interfaces that act as recording or stimulation electrodes, optical fibers, or as hollow tubes for media, e.g., fluid delivery. In other embodiments, the insertion and/or retraction device can interface with biological sensors or stimulators for placement within organisms. In still other embodiments, the insertion and/or retraction device can interface with sensors or stimulators for placement within organisms. In some embodiments, the insertion and/or retraction device can interface with micro-scale devices for placement within movably positioned sheets, gels, foams, liquids, soil, artificial organisms, organic material, composites, mixtures, and other shapes of substrate. In other embodiments, the body of the insertion and/or retraction device can be shaped into advantageous configurations for manipulation and various treatment modalities including recording, stimulating, magnetic stimulation, magnetic monitoring, fluid delivery, temperature control, optical stimulation, optical monitoring, video monitoring, and chemical irrigation of neural tissue. In some embodiments, the body that includes the tether could also serve as a delivery device for a drug, such as an antithrombotic agent, an antibiotic, an anti-inflammatory, an anti-epileptic, viral vectors, or a chemotherapeutic agent, for example. In some embodiments, the insertion and/or retraction device can place an implantable neural or non-neural interface device within any tissue within the body dependent upon the desired research or clinical result; including nervous, muscle, connective, epithelial, cardiac, lung, renal, gastrointestinal, and bone tissues. In some embodiments, the tissue is a body lumen, such as within a lumen or luminal wall of an artery or vein for example. In some embodiments, the tissue is not within a lumen and/or luminal wall. In some embodiments, an insertion device can also be used as a retraction device, and a retraction device can also be used as an insertion device. However, in some embodiments, a first device can be used for insertion, and a second device can be used for retraction. The first device and the second device can be the same or substantially the same size, shape, etc. as each other, or be different in other embodiments. In some embodiments, the device to be inserted or retracted have a compressed or low-crossing profile configuration for delivery and removal and an expanded configuration when implanted in the body. In some embodiments, the device to be inserted or retracted has the same configuration for both delivery, removal, and when implanted in the body.

In some embodiments, the insertion and/or retraction device can be interfaced with the implantable neural interface device to diagnosis and/or treat epilepsy, a movement disorder (e.g., Parkinson's Disease), a psychiatric disorder (e.g., clinical depression), the result of a stroke, Alzheimer's disease, a cognitive disorder, an anxiety disorder, an eating disorder, an addition or craving, restless leg syndrome, a sleep disorder, Tourette's syndrome, a stress disorder, coma, autism, a hearing disorder, a vision disorder, blindness, retinal degeneration, age related macular degeneration, cortical injury, optic nerve injury, dry eye syndrome, a speech disorder, amblyopia, headaches, temporomandibular joint disorder, pain (e.g., phantom limb pain and chronic pain), urinary incontinence, erectile dysfunction, bone disease, arthritis, tendonitis, the result of ligament or tendon damage, and paralysis (e.g., facial nerve paralysis and spinal paralysis). In some embodiments, the device system can be used to provide control of a prosthetic such as a limb or an external computer.

In some embodiments, the device system may wirelessly communicate with a system that is connected to a network or cloud of data. In other embodiments, the device system is connected to a biological interface to monitor tissue. In some other embodiments, the device system is connected to a biological interface to modulate tissue. In still other embodiments, the device system is connected to a biological interface to monitor and modulate tissue. In other embodiments, the biological interface can include an implantable camera.

In other embodiments, the device system can insert and/or retract a biological interface to study, diagnose, and/or treat cardiovascular conditions such as heart failure, rheumatic heart disease, hypertensive heart disease, ischemic heart disease, angina, coronary artery disease, cerebral vascular disease, stroke, atherosclerosis, cerebrovascular disease, cardiomyopathy, pericardial disease, valvular heart disease, inflammatory heart disease, congenital heart disease, and peripheral arterial disease.

In still other embodiments, the device system can insert and/or retract a biological interface to study, diagnose, and/or treat cancers, including leukemia, lymphoma, myeloma, bladder cancer, lung cancer, brain cancer, melanoma, breast cancer, non-Hodgkin lymphoma, cervical cancer, and ovarian cancer.

In other embodiments, the device system can insert and/or retract a biological interface to study, diagnose, and/or treat type 1 and type 2 diabetes. In some embodiments, the device system can include a biological interface to study, diagnose, and/or treat orthopedic conditions, including osteoarthritis, rheumatoid arthritis, bone fractures, lower back pain, neck pain, and a herniated disk.

In other embodiments, the device system can insert and/or retract a biological interface to study, diagnose, and/or treat eye conditions, including glaucoma, cataracts, age-related macular degeneration, amblyopia, diabetic retinopathy, retinal detachment, retinal tearing, and dry eye syndrome.

In still other embodiments, the device system can insert and/or retract a biological interface to study, diagnose, and/or treat hearing conditions, including hearing loss, Meniere's disease, malformation of the inner ear, autoimmune inner ear disease, tinnitus, and vertigo.

In other embodiments, the device system can insert and/or retract a biological interface to study, diagnose, and/or treat tactile disorders, including impaired sensitivity to pressure applied to the skin, elevated two-point discrimination thresholds (i.e. impaired spatial acuity), loss of vibratory sense, and deficits in proprioception.

In other embodiments, the device system can insert and/or retract biological interface to study, diagnose, and/or treat taste, taste impairing conditions, smell, and smell impairing conditions.

In still other embodiments, the device system can be movably engaged within one, two, or more body tissues, regions, or organ systems including but not limited to the scalp, skin, muscle, bone, neural tissue, heart, lungs, trachea, bronchi, diaphragm, liver, pancreas, kidneys, bladder, urethra, spleen, esophagus, stomach, intestine, penis, testes, uterus, or ovary. In some embodiments, the insertion or removal tool need not necessarily be located within a body lumen, and can be used, for example, outside of a blood vessel such as an artery or the vein. In some embodiments, about or at least about 50%, 60%, 70%, 80%, 90%, or more of a length of the insertion and/or removal tool is outside of the body or a body lumen such as a blood vessel during the insertion or removal process.

In some embodiments, systems and methods as disclosed herein can modulate neural tissue, and have a stimulatory or inhibitory effect. Neural tissue is specialized for the conduction of electrical impulses that convey information or instructions from one region of the body to another. About 98% of neural tissue is concentrated in the brain and spinal cord, which are the control centers for the nervous system. Neurons transmit signals as electrical charges which affect their cell membranes. A neuron has a cell body (soma) that contains a nucleus. The stimulus that results in the production of an electrical impulse usually affects the cell membrane of one of the dendrites, which then eventually travels along the length of an axon, which can be a meter long. Axons are often called nerve fibers with each ending at a synaptic terminal. Neuroglia are cells of the CNS (central nervous system) and PNS (peripheral nervous system) that support and protect the neurons. They provide the physical support for neural tissue by forming myelin sheaths, as well as maintaining the chemical composition of the tissue fluids and defending the tissue from infection. Schwann cells are specialized PNS cells that form myelin sheaths around neurons. Neurons (nerve cell) include a cell body that contains the nucleus and regulates the functioning of the neuron. Neurons also include axons that are cellular process (extension) that carry impulses away from the cell body. Neurons also include dendrites that are cellular process (extension) that carry impulses toward the cell body. A synapse is a space between axon of one neuron and the dendrite or cell body of the next neuron—transmits impulses from one neuron to the others. Neurotransmitters are chemicals released by axons and transmit impulses across synapses.

In some embodiments, provided is a closed loop control system for stimulating and monitoring neural activity. To meet this objective, microfilaments are embedded in various body configurations with six degrees of freedom to provide many system options for interacting with neural tissue. As an example, this would enable the data collected from a first recording microfilament (or external source) to help guide the output of a second stimulating microfilament.

The approximate diameter of circular microfilaments for conducting electrical current is between 1 μm and 250 μm, such as no more than about 25 μm, 50 μm, or 75 μm. For electrical stimulation, larger sites up to 50 μm would be advantageous to achieve surface areas that meet useful stimulation current requirements without a coating. The approximate diameter of circular microfilaments for conducting or monitoring light is between is 0.1 μm to 250 μm, such as no more than about 25 μm, 50 μm, or 75 μm. The approximate diameter of circular microfilament tubes for delivering or circulating gases, fluids, and mixtures in some embodiments is between 1 μm to 100 μm, or no more than about 50 μm, 75 μm, 100 μm, or 150 μm. Microfilaments can also be placed within a packed geometry that allows for a tapering of the penetrating area cross sections to reduce the cross sectional area and thus long term adverse neural tissue response. In some embodiments, the microfilaments can extend outward from the body's surface; these sites can be formed (e.g., bent or flattened) to provide desired functional characteristics.

The array body can take multiple forms including penetrating structures with microfilament sites and joining sections to optimize placement within the nervous system. An approximate cross sectional area of a penetrating array body in some embodiments is 1 μm$^2$ to 0.2 mm$^2$, preferably up to approximately 7850 μm$^2$. For large area coverage as in electrocorticography, larger body areas up to approximately 100 cm$^2$ or more would be advantageous to collect more data from the outer surface of a neural tissue section. In some embodiments, insertion and/or retraction devices can be used to insert or remove neural interface devices such as those disclosed in U.S. Pat. No. 9,095,267 to Halpern et al., which is hereby incorporated by reference in its entirety.

The array body can also take on non-linear shapes, which allow novel insertion techniques into difficult areas to access within surgery. A curved shape can be rotated into position where a linear angle of attack is unavailable. The array body can also have a curve located at different positions (e.g., proximal, midportion, or distal) to aid in anchoring to neural tissue or bone, while there may be a linear segment distal to, and/or proximal to the curved segment.

One advantage of the insertion and/or retraction device in some embodiments is the wide range of materials and components available to improve insertion conditions and long term performance of a microscale device within a nervous system. The components of the device can be formed from, for example, one, two, or more of gold, platinum, platinum iridium, carbon, stainless steel, steel, titanium, niobium, aluminum, conductive polymers, polymers, ceramics, organic materials or any other material depending on the desired clinical result.

Figure 1:
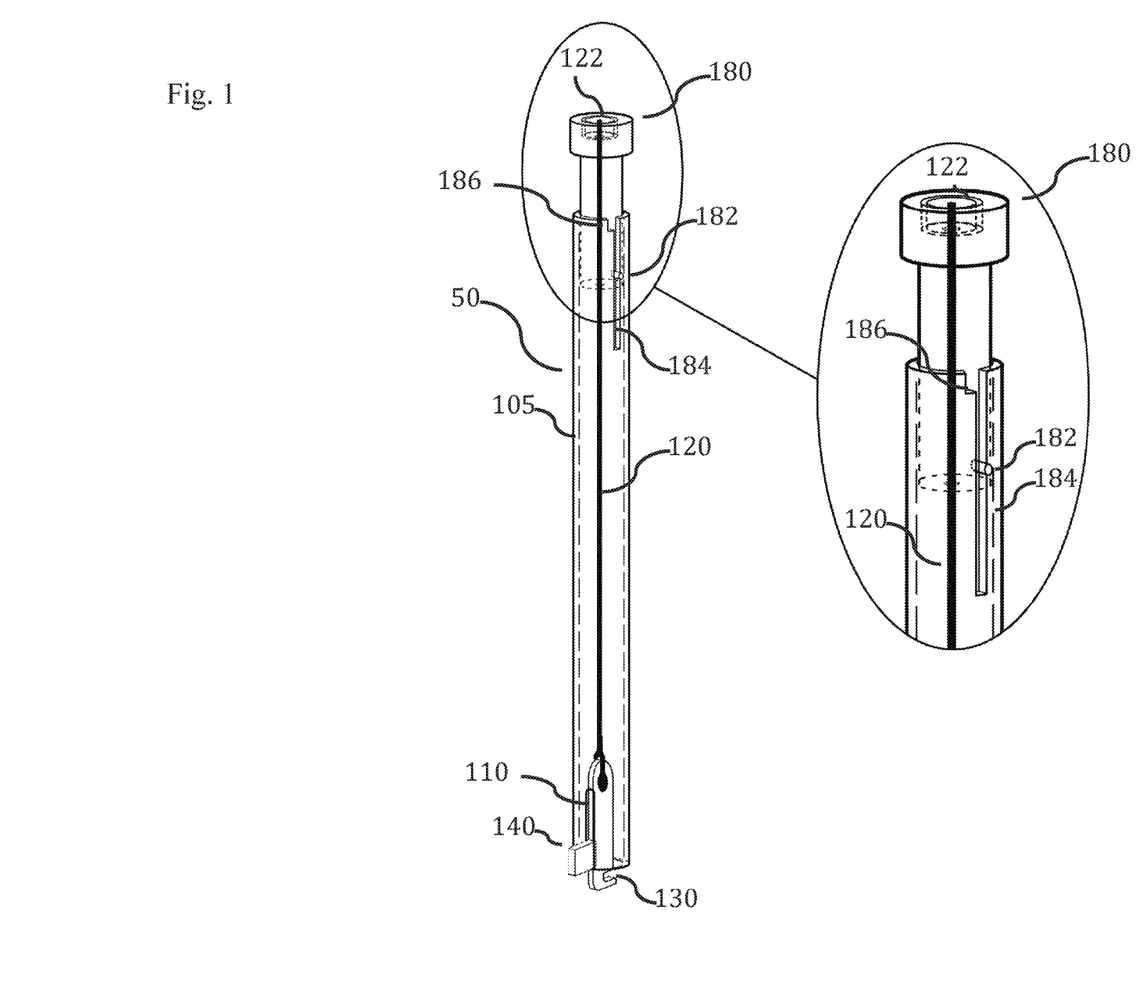
FIG. 1 shows an isometric view of an insertion device and a detail view of a control knob mechanism, according to some embodiments of the invention.

A three-dimensional view of an example of an insertion and/or retraction device 50 is shown in FIG. 1. Some embodiments of the device 50 can include, for example, a tether 120, and a continuous body 105 surrounding all or a portion of the tether 120. The continuous body can have a width of, for example, between about 5 μm and 100 μm, or no more than about 500 μm, 1000 μm, 1500 μm, 2000 μm, 2500 μm, 5000 μm, 7500 μm, or 10,000 μm. The continuous body can also have a length of between about 1 mm and 10 mm, or no more than about 25 mm, 50 mm, 75 mm, 100 mm, or 200 mm. In some embodiments, the tether 120 includes an engagement hook 130 at one end for engagement with microscale devices. In still other embodiments, an engagement loop could be positioned at one end, the tether can be integrally formed, or formed as part of a plurality of bodies joined together, so long as it is physically continuously connected together as a whole. In some embodiments, a device 50 could include an adjustable hook that can be movable to create different sized openings for engagement. In still other embodiments, the distal end of the device 50 can be shaped to provide stiffness to a flexible or hinged microscale device. In some embodiments, the continuous body 105 can be an elongate tubular member, and/or be assembled to a robotic manipulator that adjusts position based upon the movement of the targeted tissue. In still other embodiments, a control knob 180 with tracking pin feature 182 or other feature such as a wheel, lever, or the like can, for example, slide and rotate between the slot 184 communicating with or near the proximal end of the device and the tension stop 186 that relax and tension the tether 120 respectively. In some embodiments, the elasticity of the tether 120 allows for a degree of stretch sufficient for the user to pull the control knob 180 back against before rotating to a new position and allowing it to rest in a slot or track 184. In some embodiments, the slot or track 110 and/or the slot or track 184 has an axial length that is between about 1% and 50%, such as between about 1% and 20%, or between about 1% and 10% of the axial length of the continuous body 105, or in some embodiments about or less than about 50%, 40%, 30%, 20%, 10%, 5%, or less, or ranges encompassing any two of the foregoing percentages.

In other embodiments, a flap 140 can have a shape that is easier to grab by tweezers or other implements. In some other embodiments, the end effector 130 can have an automated mechanism to grab a microscale device. In still other embodiments, near the distal end of the continuous body 105 can be shaped to engage with microscale devices of different shapes. In some other embodiments, the width of the end effector can be between about 1 μm and 50 μm, or no more than about 100 μm, 500 μm, 1000 μm, 1500 μm, 2000 μm, 2500 μm, 3000 μm, or 5000 μm. In still other embodiments, the width of the opening of the end effector can be between about 1 μm and 50 μm, or no more than about 100 μm, 500 μm, 1000 μm, 1500 μm, 2000 μm, 2500 μm, 3000 μm, or 5,000 μm. In other embodiments, the width of an automated end effector can be between about 1 μm and 50 μm, or no more than about 100 μm, 500 μm, 1000 μm, 1500 μm, 2000 μm, 2500 μm, 3000 μm, or 5000 μm. In still other embodiments, the continuous body can be shaped to encourage the sliding of the tether 120 when it is movably displaced. In some other embodiments, the cross-section of tether 120 can have a shape that prevents some rotations within the continuous body 105. In other embodiments, the end effector can be any desired shape, including a shape that is threaded through an aperture on a micro-scale device. In still other embodiments, the tether can be elastic or inelastic. In some other embodiments, the aperture of the microscale device can be elastic or inelastic. In some embodiments, the tether has sufficient column strength to push the device to be inserted or removed distally. In other embodiments, an automated or non-automated end effector can operably engage and disengage with movable jaws, a movable clamp, a movable multi-headed hook, a movable anchor, a vacuum, a movable air nozzle, a movable cable, a movable loop, a movable net, a movable cup, a movable collet, a movable snake (e.g., an articulating flexible member, akin to a flexible endoscope or device used to unclog pipes), a movable coil, a movable barb, a movable snap-fit arm, a movable prong, a movable sheet, a movable strap, a movable threaded rod, a movable threaded hole, a movable anchor, a movable rod, a movable magnet, and a movable nozzle that dispenses dissolvable material.

FIG. 1 shows an isometric view of an insertion device 50 with a tether 120 housed within, and completely or partially encircled by the continuous body 105, which can be a tubular member within a central lumen configured to house the tether 120 as shown. The distal end of the tether 120 can be looped around/tied to an aperture near the proximal end of the end effector 130 as shown. The flap 140 can extend radially outwardly of a slot 110 extending proximally a distance from the distal end of the sidewall of the continuous tubular body 105. The proximal end of the tether 120 joined by a mechanical lock 122 to the control knob 180 partially housed by the continuous body 105. The control knob 180 has a tracking pin 182 that slides within track 184 extending distally a distance from the proximal end of the sidewall of the continuous tubular body 105. The slot 110 can be circumferentially in line with, or circumferentially offset from the slot or track 184 in some embodiments. The tracking pin 182 can be movably positioned to rest in tension stop 186 to apply tension to tether 120.

Figure 1A:
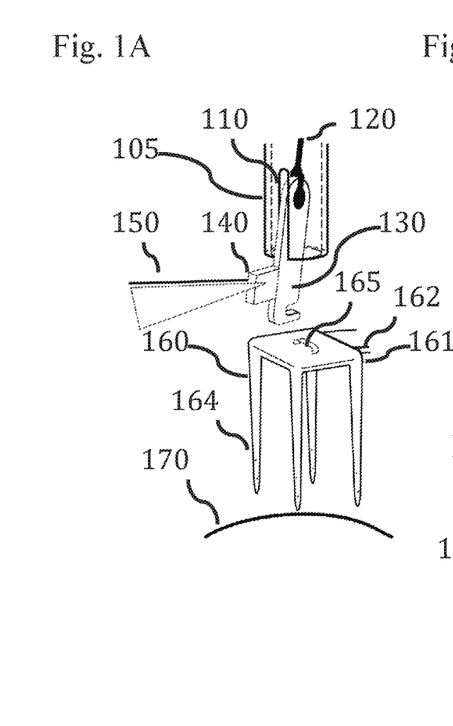
FIG. 1A shows an isometric view of an insertion device positioned above a micro-scale device with an engagement hook extended, according to some embodiments of the invention.

FIG. 1A illustrates an isometric view of an insertion device 50 with a tether 120 housed within, and encircled by the continuous body 105, which can be a tubular member within a central lumen configured to house the tether 120 as shown. The distal end of the tether 120 can be looped around/tied to an aperture near the proximal end of the end effector 130 as shown. The isometric view shows a tether 120 with wall thicknesses between about 1 μm and 25 μm, or no more than about 50 μm, 75 μm, 100 μm, 150 μm, 250 μm, 500 μm, 1000 μm, or 2000 μm in some embodiments. A pair of tweezers 150, jaws, or other tool are guiding an end effector, e.g., engagement hook 130 by grasping a hook flap or tab 140, which can extend laterally from the body of the engagement hook 130 as shown, or at other desired locations. The flap 140 can extend radially outwardly of a slot 110 extending proximally a distance from the distal end of the sidewall of the continuous tubular body 105. Beneath the insertion device distally is a microscale device 160 with shanks 164 extending substantially orthogonal to a baseplate 161 and suspended by its cable 162 above target tissue 170. The baseplate 161 has a loop 165 that can be integral to the baseplate or joined to its surface.

Figure 1B:
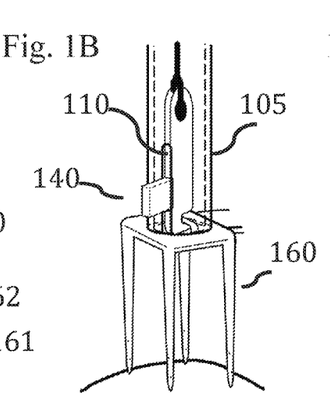
FIG. 1B shows an isometric view of an insertion device with an engagement hook and a distal end engaged with a micro-scale device, according to some embodiments of the invention.

FIG. 1B illustrates an isometric view of an insertion device with the end effector, e.g., engagement hook 130 engaged with a microscale device 160 and tensioned against the distal end of a continuous body 105. The engagement hook flap 140 extends radially outwardly of slot 110. In other embodiments the end effector could take the form of a multi-headed hook, a magnet, a vacuum nozzle, a bayonet lock mechanism, a snap fit mechanism, a press fit, and a shape for threading through an aperture on a micro-scale device for example.

Figure 1C:
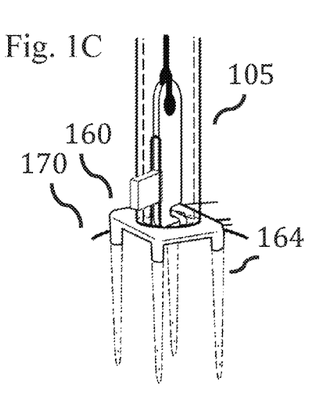
FIG. 1C shows an isometric view of an insertion device with an engagement hook and a distal end engaged with a micro-scale device inserted into tissue, according to some embodiments of the invention.

FIG. 1C illustrates an isometric view of the insertion device 50 of FIG. 1 engaged with a microscale device 160 that has been inserted into tissue 170.

Figure 1D:
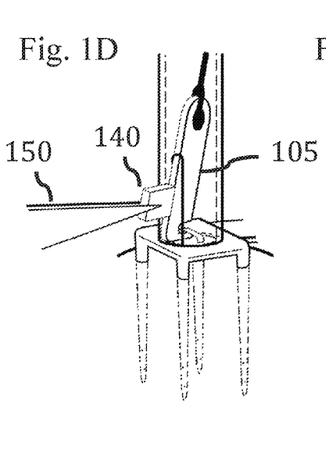
FIG. 1D shows an isometric view of tweezers displacing an engagement hook from the engagement loop of a micro-scale device, according to some embodiments of the invention.

FIG. 1D illustrates an isometric view of the insertion device 50 of FIG. 1 engaged with a microscale device 160 that has been inserted into tissue 170. Tweezers 150 grasping hook flap 140 are disengaging engagement hook 130 from a loop or other hook-engaging element on, e.g., the proximal end of the microscale device 160 in preparation for removal of the insertion device 50.

Figure 1E:
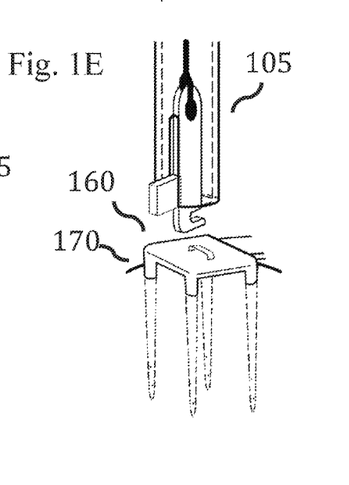
FIG. 1E shows an isometric view of an insertion device retracted away from a micro-scale device, according to some embodiments of the invention.

FIG. 1E illustrates an isometric view of an insertion device 50 retracted from, and disassociated with a microscale device 160 inserted in tissue 170. The steps illustrated in FIGS. 1B-1E could be performed in reverse order to retract a microscale device 160 previously inserted within tissue.

Figure 2:
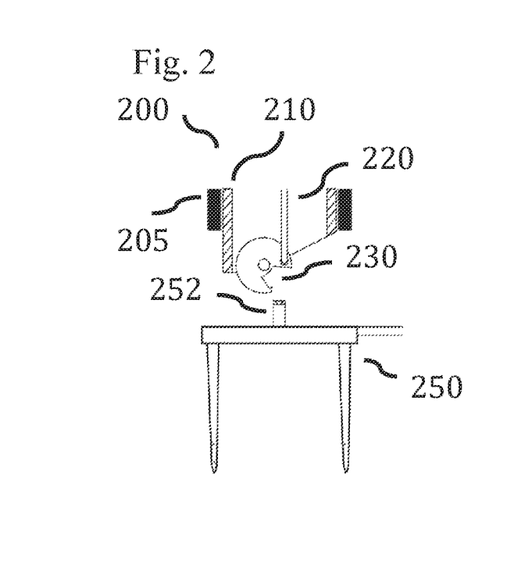
FIG. 2 shows a side view of an insertion device with an adjustable hook above a micro-scale device, according to some embodiments of the invention.

FIG. 2 illustrates a side view of the distal end of an insertion device 200 above a microscale device 250 with an engagement loop 252 configured to reversibly attach to an end effector of the insertion device. In some embodiments, the device 200 includes a pivotable engagement hook 230 and a guide rod 220 having a distal end connected to the pivotable engagement hook 230. The engagement hook 230 has fixed jaws as shown, although movable jaws are possible in other embodiments. In other embodiments the engagement hook could take the form of, for example, a four bar linkage, a sliding component, grasping jaws, a multi-headed hook, a magnetic lock, a vacuum head, a bayonet lock mechanism, a snap fit mechanism, an actuated press fit, and an articulated snaking mechanism.

Figure 2A:
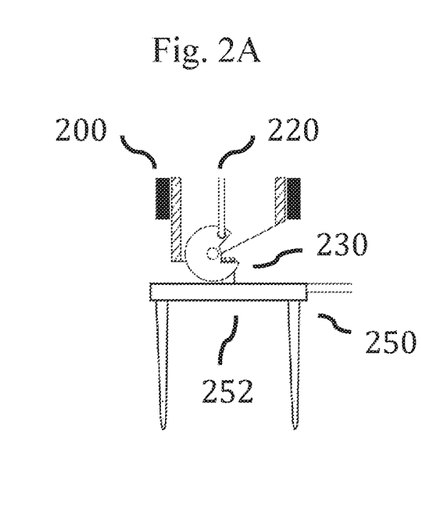
FIG. 2A shows a side view of an insertion device with an adjustable hook engaged with a micro-scale device, according to some embodiments of the invention.

FIG. 2A illustrates a side view of the insertion device 200 of FIG. 2 with a pivotable engagement hook 230 engaged with an engagement loop 252 due to the displacement of guide rod 220.

Figure 2B:
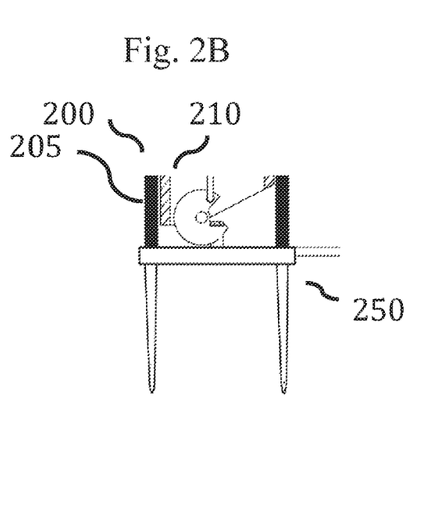
FIG. 2B shows a side view of an insertion device with an adjustable hook tensioning a micro-scale device against the distal end of the insertion device, according to some embodiments of the invention.

FIG. 2B illustrates a side view of the insertion device 200 of FIG. 2 with an engagement hook 230 on a pivot and engaged with an engagement loop 252. In some embodiments, a guide rod 220 has retracted an inner housing 210, such as an inner tubular member, to tension a microscale device 250 against the distal end of the insertion device 200 (e.g., the distal end of the continuous body outer housing). In some embodiments, the microscale device 250 could be flexible. In still other embodiments, the microscale device could include a single shank. In other embodiments, the microscale device could be a device that emits energy, including light and/or magnetic fields.

Figure 3:
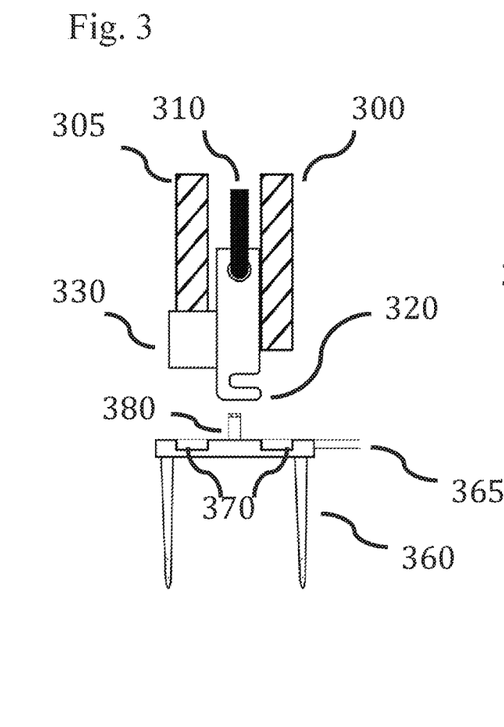
FIG. 3 shows a side view of an insertion device with an extended engagement hook above a micro-scale device with a flexible hinged backplate, according to some embodiments of the invention.

FIG. 3 illustrates a side view of an insertion device 300 with a tether member 310 encircled within a lumen of the continuous body 305. The side view shows tether 310 with thicknesses between about 1 μm and 25 μm, or no more than about 50 μm, 75 μm, 100 μm, 150 μm, 250 μm, 500 μm, 1000 μm, or 2000 μm in some embodiments. An end effector, e.g., engagement hook 320 is connected near its proximal end via an aperture or other connection to the distal end of the tether 310, such as via a loop in the tether. The insertion device 300 is shown extended above a microscale device 360 suspended by its cable 365. In some embodiments, microscale device 360 can be without a cable 365.

Figure 3A:
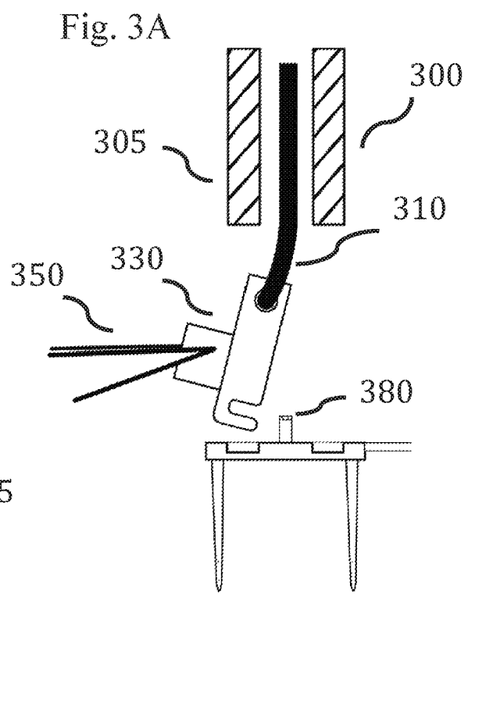
FIG. 3A shows a side view of an insertion device with tweezers displacing an extended engagement hook, according to some embodiments of the invention.

FIG. 3A illustrates a side view of the insertion device 300 of FIG. 3 with a tether 310 encircled by, and the distal end of the tether 310 is extending distally with respect to the continuous body 305. The side view shows a pair of tweezers 350, jaws, or other tool grasping a hook flap or tab 330 which can extend laterally from the body of the engagement hook 320 as shown, or at other desired locations and guide an engagement hook 320. The tool 350 can actuate the tab 330 in a desired direction in order to move the engagement hook 320 in an appropriate direction. Beneath the insertion device is a microscale device 360 suspended by or otherwise attached to its cable 365. In some embodiments, the microscale device 360 has hinges 370 for flexibility.

Figure 3B:
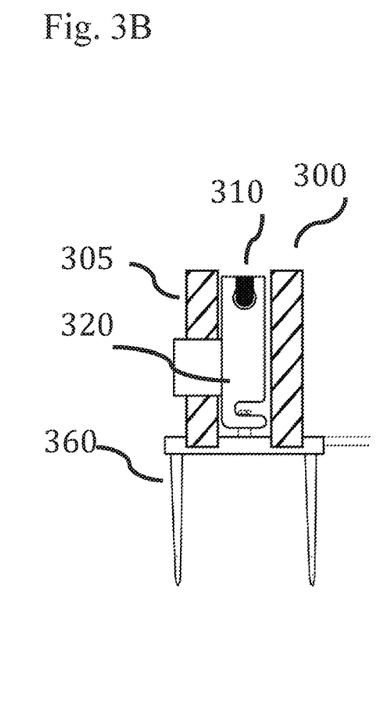
FIG. 3B shows a side view of an insertion device with an engagement hook tensioning a micro-scale device with a flexible hinged backplate against the distal end of the insertion device, according to some embodiments of the invention.

FIG. 3B illustrates a side view of the insertion device 300 of FIG. 3 with a tether 310 encircled by a continuous body 305. The side view shows an engagement hook 320 inserted within engagement loop 380, aperture, or other complementary connector on the microscale device 360, such as on a proximal baseplate of the microscale device 360. A tether 310 can tension the microscale device 360 against the distal end of continuous body 305. In some embodiments, the distal end of the continuous body 305 engages the hinges 370 of the microscale device, stiffening the microscale device 360 for insertion into tissue. In still other embodiments the distal end of the continuous body 305 has bosses that insert into holes in a flexible microscale device. In other embodiments, the insertion device mechanically stiffens the microscale device by engaging it from one or more sides. In still other embodiments the insertion device uses a vacuum or magnetic attraction to engage a microscale device.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method of inserting a micro-scale device into a target substrate, comprising:
    providing an insertion tool comprising a tether having a proximal end, a distal end, and an elongate body, and an end effector operably connected to the distal end of the tether;
    mechanically coupling the end effector to a portion of the micro-scale device;
    positioning the micro-scale device at a desired location within a target substrate;
    mechanically decoupling the end effector from the micro-scale device;
    withdrawing the insertion tool from the target substrate, and
    monitoring the motion of a nonstationary target surface, wherein positioning the micro-scale device comprises adjusting the positioning speed as a function of the monitored motion of the target surface.

2. The method of claim 1, wherein positioning the micro-scale device at a desired location comprises moving the end effector distally with respect to a housing of the insertion tool.

3. The method of claim 2, wherein the housing comprises a tubular body comprising a central lumen.

4. The method of claim 1, wherein the end effector comprises a hook on its distal end.

5. The method of claim 1, wherein the end effector comprises a releasable connector.

6. The method of claim 4, wherein the micro-scale device comprises a neural interface or a biological interface.

7. The method of claim 4, wherein mechanically coupling the end effector to a portion of the micro-scale device comprises positioning the hook through an aperture on the micro-scale device.

8. The method of claim 4, wherein mechanically decoupling the end effector to a portion of the micro-scale device comprises disassociating the hook from an aperture on the micro-scale device.

9. The method of claim 1, wherein the target substrate is non-stationary.

10. The method of claim 6, wherein the target substrate comprises neural tissue.

11. The method of claim 1, wherein mechanically coupling the end effector to a portion of the micro-scale device does not substantially displace the microscale device.

12. The method of claim 1, wherein positioning comprises manipulating a tab on the end effector.

13. The method of claim 1, wherein positioning the micro-scale device comprises actuating a control on the proximal end of the device to move the tether with respect to the elongate body.

14. The method of claim 13, wherein actuating a control comprises rotating a control knob in a direction, thereby moving a tracking pin axially distally within a slot oriented substantially parallel to the longitudinal axis of the elongate body.

15. The method of claim 1, wherein the tether is elastic.

16. The method of claim 7, wherein a sidewall of the aperture is elastic.

17. A method of inserting a micro-scale device into a target substrate, comprising:
    providing an insertion tool comprising a tether having a proximal end, a distal end, and an elongate body, and an end effector operably connected to the distal end of the tether, wherein the tether is elastic;
    mechanically coupling the end effector to a portion of the micro-scale device;
    positioning the micro-scale device at a desired location within a target substrate;
    mechanically decoupling the end effector from the micro-scale device; and
    withdrawing the insertion tool from the target substrate.

18. The method of claim 17, wherein positioning the micro-scale device at a desired location comprises moving the end effector distally with respect to a housing of the insertion tool.

19. The method of claim 18, wherein the housing comprises a tubular body comprising a central lumen.

20. The method of claim 17, wherein the end effector comprises a hook on its distal end.

21. The method of claim 17, wherein the end effector comprises a releasable connector.

22. The method of claim 20, wherein the micro-scale device comprises a neural interface or a biological interface.

23. The method of claim 20, wherein mechanically coupling the end effector to a portion of the micro-scale device comprises positioning the hook through an aperture on the micro-scale device.

24. The method of claim 20, wherein mechanically decoupling the end effector to a portion of the micro-scale device comprises disassociating the hook from an aperture on the micro-scale device.

25. The method of claim 17, wherein the target substrate is non-stationary.

26. The method of claim 22, wherein the target substrate comprises neural tissue.

27. The method of claim 17, wherein mechanically coupling the end effector to a portion of the micro-scale device does not substantially displace the microscale device.

28. The method of claim 17, further comprising monitoring the motion of the nonstationary target surface.

29. The method of claim 17, wherein positioning comprises manipulating a tab on the end effector.

30. The method of claim 17, wherein positioning the micro-scale device comprises actuating a control on the proximal end of the device to move the tether with respect to the elongate body.

31. The method of claim 30, wherein actuating a control comprises rotating a control knob in a direction, thereby moving a tracking pin axially distally within a slot oriented substantially parallel to the longitudinal axis of the elongate body.

32. The method of claim 23, wherein a sidewall of the aperture is elastic.

33. A method of inserting a micro-scale device into a target substrate, comprising:
    providing an insertion tool comprising a tether having a proximal end, a distal end, and an elongate body, and an end effector operably connected to the distal end of the tether, wherein the end effector comprises a hook on its distal end;
    mechanically coupling the end effector to a portion of the micro-scale device, wherein mechanically coupling the end effector to a portion of the micro-scale device comprises positioning the hook through an aperture on the micro-scale device, wherein a sidewall of the aperture is elastic;
    positioning the micro-scale device at a desired location within a target substrate;
    mechanically decoupling the end effector from the micro-scale device; and
    withdrawing the insertion tool from the target substrate.

34. The method of claim 33, wherein positioning the micro-scale device at a desired location comprises moving the end effector distally with respect to a housing of the insertion tool.

35. The method of claim 34, wherein the housing comprises a tubular body comprising a central lumen.

36. The method of claim 33, wherein the end effector comprises a releasable connector.

37. The method of claim 33, wherein the micro-scale device comprises a neural interface or a biological interface.

38. The method of claim 33, wherein mechanically decoupling the end effector to a portion of the micro-scale device comprises disassociating the hook from an aperture on the micro-scale device.

39. The method of claim 33, wherein the target substrate is non-stationary.

40. The method of claim 37, wherein the target substrate comprises neural tissue.

41. The method of claim 33, wherein mechanically coupling the end effector to a portion of the micro-scale device does not substantially displace the microscale device.

42. The method of claim 33, further comprising monitoring the motion of the nonstationary target surface.

43. The method of claim 33, wherein positioning comprises manipulating a tab on the end effector.

44. The method of claim 33, wherein positioning the micro-scale device comprises actuating a control on the proximal end of the device to move the tether with respect to the elongate body.

45. The method of claim 44, wherein actuating a control comprises rotating a control knob in a direction, thereby moving a tracking pin axially distally within a slot oriented substantially parallel to the longitudinal axis of the elongate body.

* * * * *